United States Patent
Govari et al.

(10) Patent No.: US 11,672,952 B2
(45) Date of Patent: Jun. 13, 2023

(54) FINDING ELONGATION OF EXPANDABLE DISTAL END OF CATHETER

(71) Applicant: Biosense Webster (Israel) Ltd., Yokneam (IL)

(72) Inventors: Assaf Govari, Haifa (IL); Avigdor Rosenberg, Kiryat Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 974 days.

(21) Appl. No.: 16/234,604

(22) Filed: Dec. 28, 2018

(65) Prior Publication Data

US 2020/0206461 A1     Jul. 2, 2020

(51) Int. Cl.
*A61M 25/01*     (2006.01)
*A61B 34/20*     (2016.01)
(Continued)

(52) U.S. Cl.
CPC ......... *A61M 25/0105* (2013.01); *A61B 5/062* (2013.01); *A61B 34/20* (2016.02);
(Continued)

(58) Field of Classification Search
CPC .......... A61M 25/0105; A61M 25/0074; A61M 25/10; A61M 2025/0166; A61M 25/0108;
(Continued)

(56) References Cited

U.S. PATENT DOCUMENTS 5,391,199 A     2/1995    Ben-Haim
6,239,724 B1     5/2001    Doron et al.
(Continued)

FOREIGN PATENT DOCUMENTS

EP            2579767 A2     4/2013
WO          96/05768 A1     2/1996
WO    WO 2011/159600 A2    12/2011

OTHER PUBLICATIONS

Feuerstein et al.; Magneto-Optical Tracking of Flexible Laparoscopic Ultrasound: Model-Based Online Detection and Correction of Magnetic Tracking Errors; IEEE Transactions On Medical Imaging; vol. 28, No. 6; Jun. 2009; pp. 951-961.
(Continued)

*Primary Examiner* — Sanjay Cattungal
(74) *Attorney, Agent, or Firm* — Troutman Pepper Hamilton Sanders LLP

(57) ABSTRACT

A system includes an expandable distal-end assembly, a proximal position sensor, a distal position sensor, and a processor. The expandable distal-end assembly is coupled to a distal end of a shaft for insertion into a cavity of an organ of a patient. The proximal and distal position sensors are located at a proximal end and a distal end of the distal-end assembly, respectively. The processor is configured to estimate a position and a longitudinal direction of the proximal sensor, and a position of the distal sensor, all in a coordinate system used by the processor. The processor is further configured to project the estimated position of the distal sensor on an axis defined by the estimated longitudinal direction, and calculate an elongation of the distal-end assembly by calculating a distance between the estimated position of the proximal sensor and the projected position of the distal sensor.

14 Claims, 2 Drawing Sheets

(51) Int. Cl.
    *A61B 5/06* (2006.01)
    *A61M 25/00* (2006.01)
    *A61M 25/10* (2013.01)

(52) U.S. Cl.
    CPC . *A61M 25/0074* (2013.01); *A61B 2034/2061* (2016.02); *A61B 2560/0223* (2013.01); *A61M 25/10* (2013.01); *A61M 2025/0166* (2013.01)

(58) Field of Classification Search
    CPC . A61B 5/062; A61B 34/20; A61B 2034/2061; A61B 2560/0223; A61B 5/318; A61B 5/287; A61B 5/066; A61B 2017/00243; A61B 2034/2051; A61B 2562/0223; A61B 5/6853; A61B 5/6858; A61B 5/065; A61B 5/6859; A61B 2034/2072
    See application file for complete search history.

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,748,255 B2 | 6/2004 | Fuimaono et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2006/0009690 A1 | 1/2006 | Fuimaono et al. |
| 2007/0106114 A1* | 5/2007 | Sugimoto .............. A61B 5/068 600/117 |
| 2011/0313414 A1* | 12/2011 | Liu ........................ A61B 5/062 606/41 |
| 2013/0123694 A1 | 5/2013 | Subramaniyan et al. |
| 2015/0150472 A1* | 6/2015 | Harlev .................. A61B 5/287 600/374 |
| 2015/0366485 A1* | 12/2015 | Kassab ................ A61B 5/6886 600/373 |
| 2016/0281490 A1* | 9/2016 | Samuel .................... E21B 7/10 |
| 2019/0033061 A1* | 1/2019 | Onishi ................. G01B 5/0014 |
| 2020/0206461 A1* | 7/2020 | Govari .................. A61B 5/287 |

OTHER PUBLICATIONS

European Search Report and Written Opinion issued in in Application No. EP 19219613; dated May 22, 2020; 8 pages.
Partial European Search Report issued in Application No. EP 19219613; dated Jun. 2, 2020; 13 pages.
Extended European Search Report issued in Application No. EP 19219613; dated Sep. 14, 2020; 10 pages.

* cited by examiner

FINDING ELONGATION OF EXPANDABLE DISTAL END OF CATHETER

FIELD OF THE INVENTION

The present invention relates generally to invasive medical probes, and particularly to cardiac catheters.

BACKGROUND OF THE INVENTION

Tracking a shape of intrabody objects, such as catheters is known in the patent literature. For example, U.S. Pat. No. 6,748,255 describes an improved basket catheter that is particularly useful for mapping the heart. The catheter comprises an elongated catheter body having proximal and distal ends and at least one lumen therethrough. A basket-shaped electrode assembly is mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body. The catheter further comprises a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the spines of the basket-shaped mapping assembly to find the positions of the at least one electrode of each spine.

As another example, U.S. Patent Application Publication 2013/0123694 describes a method for measuring balloon expansion profile in vivo. The method comprises providing a balloon with at least one sensing element as a diagnostic device, where the at least one sensing element is characterized by at least one attribute that is representative of balloon dimension; measuring the at least one attribute to obtain an observed attribute value; and estimating the balloon dimension and the balloon expansion profile based on the observed attribute value. A diagnostic kit for measuring a balloon expansion profile in vivo is also provided. The diagnostic kit comprises the diagnostic device; a measurement module for measuring an observed attribute value for the attribute; and a processor module for processing the observed attribute value to estimate the balloon expansion profile as one or more outputs.

U.S. Patent Application Publication 2011/0313414 describes a method for simulating the bend shape of a catheter including providing at least two sensor elements in the catheter, wherein the sensor elements traverse magnetic line of force to generate induced current. Space information of the sensor elements is extracted from the induced current information, and the bend shape of the catheter is calculated according to aforementioned space information in combination with characteristic information of the catheter.

SUMMARY OF THE INVENTION

An embodiment of the present invention provides a system, including an expandable distal-end assembly, a proximal position sensor, a distal position sensor, and a processor. The expandable distal-end assembly is coupled to a distal end of a shaft for insertion into a cavity of an organ of a patient. The proximal position sensor is located at a proximal end of the distal-end assembly. The distal position sensor is located at a distal end of the distal-end assembly. The processor is configured to, based on signals received from the proximal position sensor, estimate a position and a longitudinal direction of the proximal sensor in a coordinate system used by the processor, and, based on signals received from the distal position sensor, estimate a position of the distal position sensor in the coordinate system. The processor is further configured to project the estimated position of the distal position sensor on an axis defined by the estimated longitudinal direction, and calculate an elongation of the distal-end assembly by calculating a distance between the estimated position of the proximal position sensor and the projected position of the distal position sensor.

In some embodiments, the proximal position sensor and the distal position sensor are magnetic sensors.

In some embodiments, using the calculated elongation, the processor is further configured to estimate an ellipticity of the expandable distal-end assembly.

In an embodiment, the expandable distal-end assembly includes a basket. In another embodiment, the expandable distal-end assembly includes a balloon.

In some embodiments, the processor is configured to, based on calculating the elongation, indicate a degree of elongation of the expandable distal-end assembly.

There is additionally provided, in accordance with an embodiment of the present invention, a method, including, in a processor, receiving signals from a proximal position sensor located at a proximal end of an expandable distal-end assembly coupled to a distal end of a shaft for insertion into a cavity of an organ of a patient, and from a distal position sensor located at a distal end of the distal-end assembly. Based on the signals received from the proximal position sensor, a position and a longitudinal direction of the proximal position sensor are estimated in a coordinate system used by the processor. Based on the signals received from the distal position sensor, a position of the distal position sensor in the coordinate system is estimated. The estimated position is projected on an axis defined by the estimated longitudinal direction. An elongation of the distal-end assembly is calculated by calculating a distance between the estimated position of the proximal sensor and the projected position of the distal position sensor.

There is further provided, in accordance with an embodiment of the present invention, a system including an expandable distal-end, a proximal position device, a distal position device, and a processor. The expandable distal-end assembly is coupled to a distal end of a shaft for insertion into a cavity of an organ of a patient. The proximal position device is located at a proximal end of the distal-end assembly. The distal position device is located at a distal end of the distal-end assembly, whereas one of the position devices is configured as a transmitter and the other as a receiver. The processor is configured to, based on signals received from the receiver, estimate a distance of the receiver from the transmitter, and indicate an elongation of the expandable distal-end assembly as the calibrated distance.

There is furthermore provided, in accordance with an embodiment of the present invention, a method, including communicating signals between a proximal position device located at a proximal end of an expandable distal-end assembly coupled to a distal end of a shaft for insertion into a cavity of an organ of a patient, and a distal position device located at a distal end of the distal-end assembly, wherein one of the position devices is configured as a transmitter and the other as a receiver. Based on the communicated signals received from the receiver, a distance of the receiver from the transmitter is estimated. An elongation of the distal-end assembly catheter is indicated as the calibrated distance.

The present invention will be more fully understood from the following detailed description of the embodiments thereof, taken together with the drawings in which:

DETAILED DESCRIPTION OF EMBODIMENTS

Overview

Figure 1:
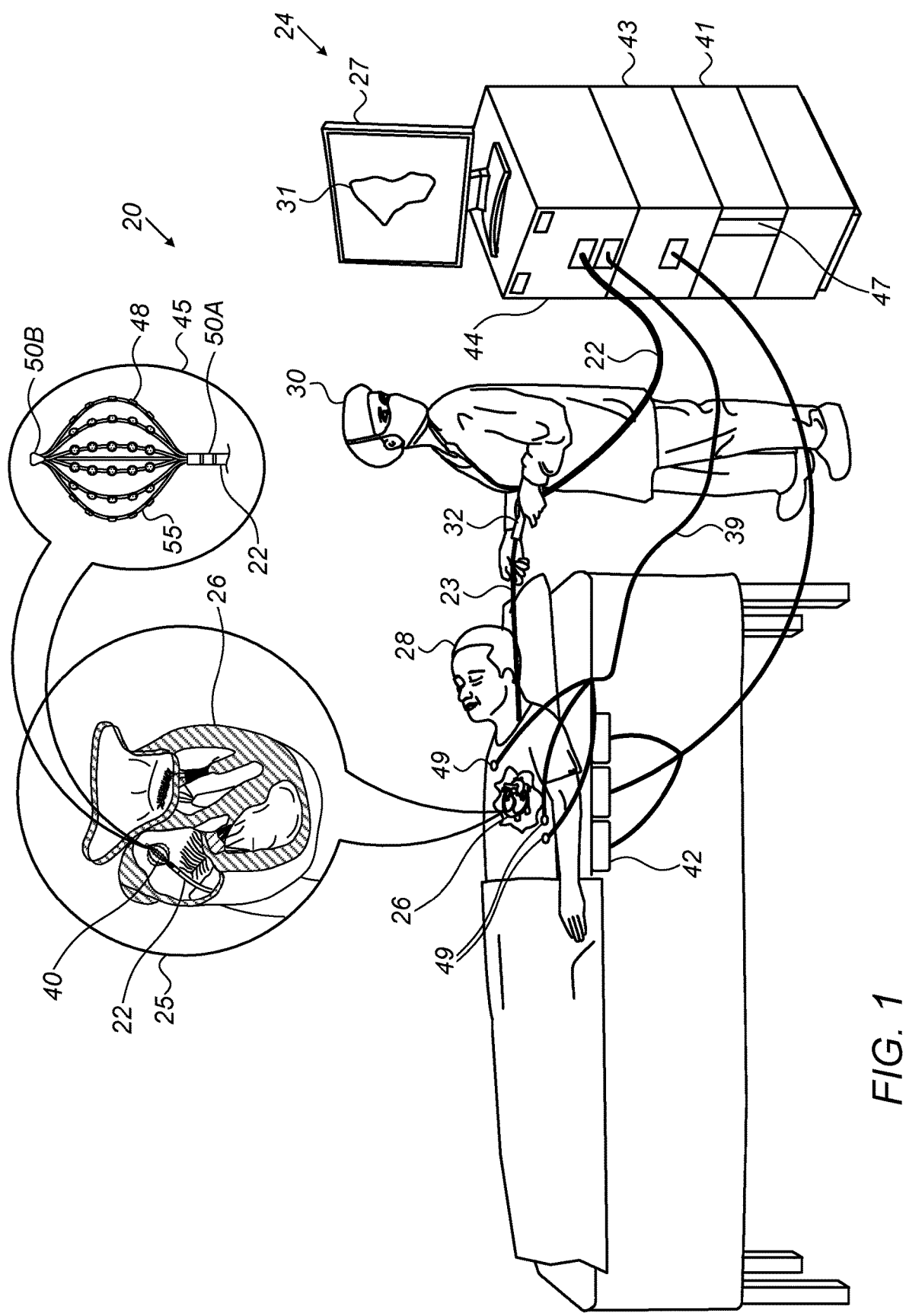
FIG. 1 is a schematic, pictorial illustration of a system for electro-anatomical mapping comprising a basket catheter, in accordance with an embodiment of the present invention.

An expandable distal-end assembly of a catheter for insertion into a cavity of an organ of a patient, such as basket or balloon catheter, may be employed in various clinical applications, such as electro-anatomical mapping and ablation of the cavity walls, e.g., cardiac chamber walls. The deployment of the expandable distal-end assembly, which is coupled to a distal end of a shaft for insertion, is usually accomplished manually. Thus, it is difficult to know the exact measure of the expandable distal-end assembly shape, such as basket or balloon ellipticity, inside the cavity, as there is little (e.g., indirect) indication whether the expandable distal-end assembly has fully expanded inside the cavity (e.g., a degree of elongation of the expandable distal-end assembly).

When, for example, basket ellipticity is not well known, measurement results relying on a known ellipticity may produce distorted results. For example, signals from ultrasound transducers that are fitted on a plurality of expandable spines of the basket may be calibrated incorrectly due to a wrongly assumed basket ellipticity that, for example, causes error in assumed relative positions and orientations of the ultrasound transducers, and may cause a processor to produce a distorted anatomical map of the cavity.

In another example, when using a balloon catheter, it is important to know whether the balloon is in fully expanded, fully collapsed or in some intermediate state, before taking action such as performing ablation, inflating the balloon or retracting it into the sheath.

Embodiments of the present invention that are described hereinafter provide tracking systems and methods for estimating an elongation of the expandable distal-end assembly, from which the expandable distal-end assembly shape, and hence relative positions and orientations of devices fitted on, for example, expandable spines of the expandable distal-end assembly, can be more accurately estimated by a processor. One disclosed embodiment incorporates an estimation-error correction technique using projection, as described below.

In some embodiments, a tracking system tracks an expandable distal-end assembly of a catheter, the expandable distal-end assembly comprising a proximal position and direction sensor located at a proximal end of the expandable distal-end assembly and a distal position sensor located at a distal end of the expandable distal-end assembly. A processor is configured (e.g., programmed) to estimate a position and a longitudinal direction of the proximal sensor in a coordinate system used by the tracking system, based on signals received from the proximal position sensor.

Based on signals received from the distal position sensor, the processor estimates a position of the distal sensor in the coordinate system, and, to reduce an estimation-error in that position, corrects the estimated position of the distal sensor by projecting the estimated position on an axis defined by the estimated longitudinal direction.

Then, the processor calculates an elongation of the expandable distal-end assembly (e.g., basket or balloon catheter) by calculating the distance between the estimated position of the proximal sensor and the projected position of the distal sensor. Based on the calculated elongation, the processor estimates, for example, the ellipticity of the basket and/or the elongation state of the basket or of the balloon.

In an embodiment, the proximal and distal sensors are magnetic sensors. The sensors are operated by a catheter-based tracking system, such as the CARTO3® (made by Biosense-Webster, Irvine, Calif.). In another embodiment, two position devices are provided, where one position device is located at a proximal end of the expandable distal-end assembly and the other position device is located at a distal end of the distal-end assembly. one of the position devices is configured as a transmitter and the other as a receiver. Based on signals received from the receiver, and based on an available calibration of inter-position device distance as a function of the received signal, the processor estimates the distance of the receiver sensor from the transmitter sensor. The processor then provides an elongation of the expandable distal-end assembly as the estimated calibrated distance.

Typically, the processor is programmed in software containing a particular algorithm that enables the processor to conduct each of the processor related steps and functions outlined above.

The disclosed systems and methods for finding elongation of an expandable distal-end assembly of catheter using projection inside a cavity of an organ may improve diagnostic and/or treatment results of a catheterization procedure done using the expandable distal-end assembly catheter.

System Description

FIG. 1 is a schematic, pictorial illustration of an electro-anatomical mapping system 20, in accordance with an embodiment of the present invention. A physician 30 navigates a basket catheter 40 (made by Biosense-Webster), seen in detail in inset 45, to a target location in a heart 26 of a patient 28, by manipulating shaft 22, using a manipulator 32 near the proximal end of the catheter, and/or deflection from a sheath 23. In the embodiment seen in inset 25, physician 30 uses catheter 40 to perform electro-anatomical mapping of a cardiac chamber.

The embodiments described herein refer mainly to a basket distal-end assembly, purely by way of example. In alternative embodiments, the disclosed techniques can be used for estimating the elongation (and thus the degree of expansion) of a balloon-based distal-end assembly or of any other suitable type of expandable distal-end assembly.

Catheter 40 is inserted in a folded configuration, through sheath 23, and only after the catheter exits sheath 23 does catheter 40 regain its intended functional shape. By containing catheter 40 in a folded configuration, sheath 23 also serves to minimize vascular trauma on its way to the target location.

Basket catheter 40 incorporates a magnetic sensor 50A, seen in inset 45, at the distal edge of shaft 22 (i.e., at the proximal edge of basket catheter 40). Typically, although not necessarily, sensor 50A is a Triple-Axis Sensor (TAS). A second magnetic sensor 50B is included in a distal edge of the basket catheter. Sensor 50B may be a Single-Axis Sensor (SAS) or a Triple-Axis Sensor (TAS), for example.

Catheter 40 further comprises multiple expandable spines 55, which may be mechanically flexible, to each of which are coupled one or more devices 48. Devices 48 may be of numerous types, such as sensing-electrodes, ablation-electrodes, ultrasound transducers, contact force sensors, irrigation ports, temperature sensors, and others. Magnetic sensors 50A and 50B and devices 48 are connected by wires running through shaft 22 to various driver circuitries in a console 24. Alternatively, as noted above, catheter 40 may be an inflatable balloon.

In some embodiments, system 20 comprises a magnetic-sensing sub-system to estimate an ellipticity of basket catheter 40, as well as its elongation/retraction state, inside a cardiac chamber of heart 26 by estimating the elongation of basket catheter 40 from the distance between sensors 50A and 50B. Patient 28 is placed in a magnetic field generated by a pad containing magnetic field generator coils 42, which are driven by unit 43. The magnetic fields generated by coils 42 generate signals in sensors 50A and 50B, which are indicative of position and/or direction. The generated signals are transmitted to console 24 and become corresponding electrical inputs to a processor 41. The processor uses the signals to calculate the elongation of basket catheter 40, and to estimate basket ellipticity and elongation/retraction state from the calculated distance between sensors 50A and 50B.

The method of position and/or direction sensing using external magnetic fields and magnetic sensors, such as 50A and 50B, is implemented in various medical applications, for example, in the CARTO™ system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference and attached hereto in the Appendix.

Processor 41, typically a general-purpose computer, is further connected via suitable front end and interface circuits 44, to receive signals from surface-electrodes 49. Processor 41 is connected to surface-electrodes 49 by wires running through a cable 39 to the chest of patient 28.

In an embodiment, processor 41 additionally receives various spatial and electrophysiological signals via an electrical interface 44, and uses the information contained in these signals to construct an electro-anatomical map 31 of the cavity. During and/or following the procedure, processor 41 may display electro-anatomical map 31 on a display 27.

Processor 41 is typically programmed in software by one skilled in this art to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables processor 41 to perform the disclosed steps, as described below.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Finding Basket Catheter Elongation Using Projection

Figure 2:
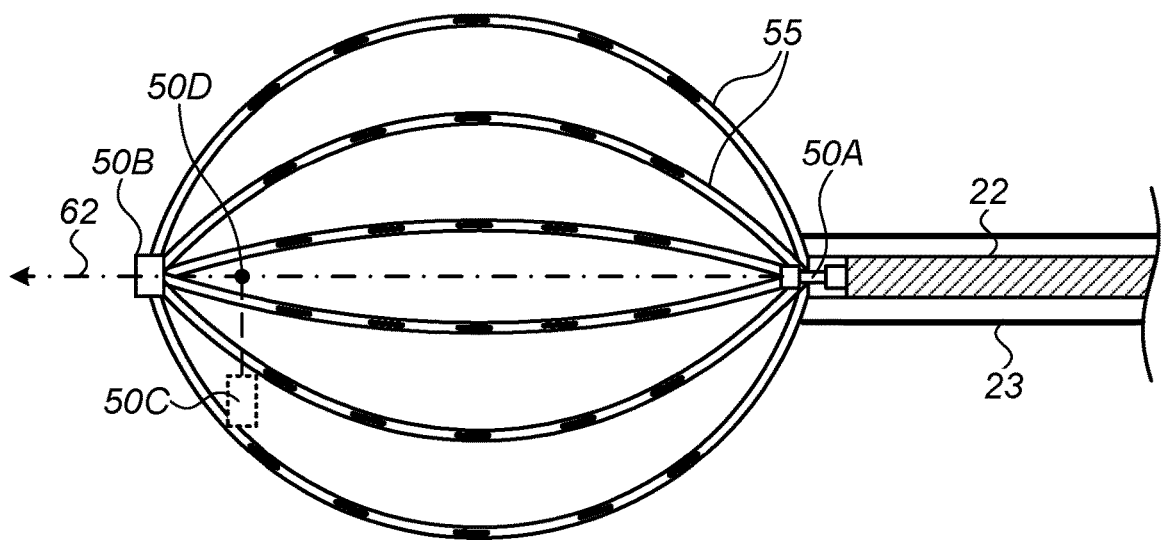
FIG. 2 is a schematic side-view of the basket catheter of FIG. 1, in accordance with embodiments of the present invention.

FIG. 2 is a schematic side-view of basket catheter 40 of FIG. 1, in accordance with embodiments of the present invention. The expandable frame of basket catheter 40 comprises a plurality of expandable spines 55 coupled to a distal end of shaft 22, in proximity to the location of proximal position and direction sensor 50A. The expandable frame of basket catheter 40 extends along a longitudinal axis 62 and converges at a distal end of the basket, the location of distal position sensor 50B.

Spines 55 form an ellipsoid shape of the basket, such as one defined by a surface of revolution about longitudinal axis 62. In general, however, the basket and devices mounted on spines are not required to have a full rotational symmetry.

Based on signals from sensor 50A, processor 41 estimates longitudinal direction 62 (i.e., a direction which is parallel to a longitudinal axis defined by the distal end of shaft 22). At the same time, processor 41 estimates, potentially incorrectly, a position of distal sensor 50B, as being position 50C. Evidently, such an error would cause the estimated shape of the basket to be distorted. The error is largely amended by processor 41 projecting the coordinates of incorrect position 50C on axis 62, so as to obtain a projected position 50D, which is more accurate. Based on the distance along axis 62 between positions 50A and 50D, the processor derives actual values of elongation and ellipticity.

In another embodiment, proximal sensor 50A is replaced with a position device that is configured as a transmitter and distal sensor 50B is replaced with a position device that is configured as a receiver. Based on signals received from the receiver, and based on an available calibration of inter-position-device distance as a function of the received signal, the processor estimates the distance of the receiver sensor from the transmitter. The processor then provides an elongation of the basket as the estimated calibrated distance.

In general, a method is provided, which comprises communicating signals between a proximal position device located at a proximal end of an expandable basket coupled to a distal end of a shaft for insertion into a cavity of an organ of a patient, and a distal position device located at a distal end of the basket, wherein one of the position devices is configured as a transmitter and the other as a receiver The illustration in FIG. 2 is conceptual and brought by way of example. The actual basket structure may vary. For example, expandable spines 55 may be made of a printed circuit board (PCB), or of a shape memory alloy. More generally, the illustration shown in FIG. 2 is applicable, with the necessary changes have been made, to any expandable distal-end assembly of a catheter for insertion into a cavity of an organ of a patient, such as a balloon catheter.

Figure 3:
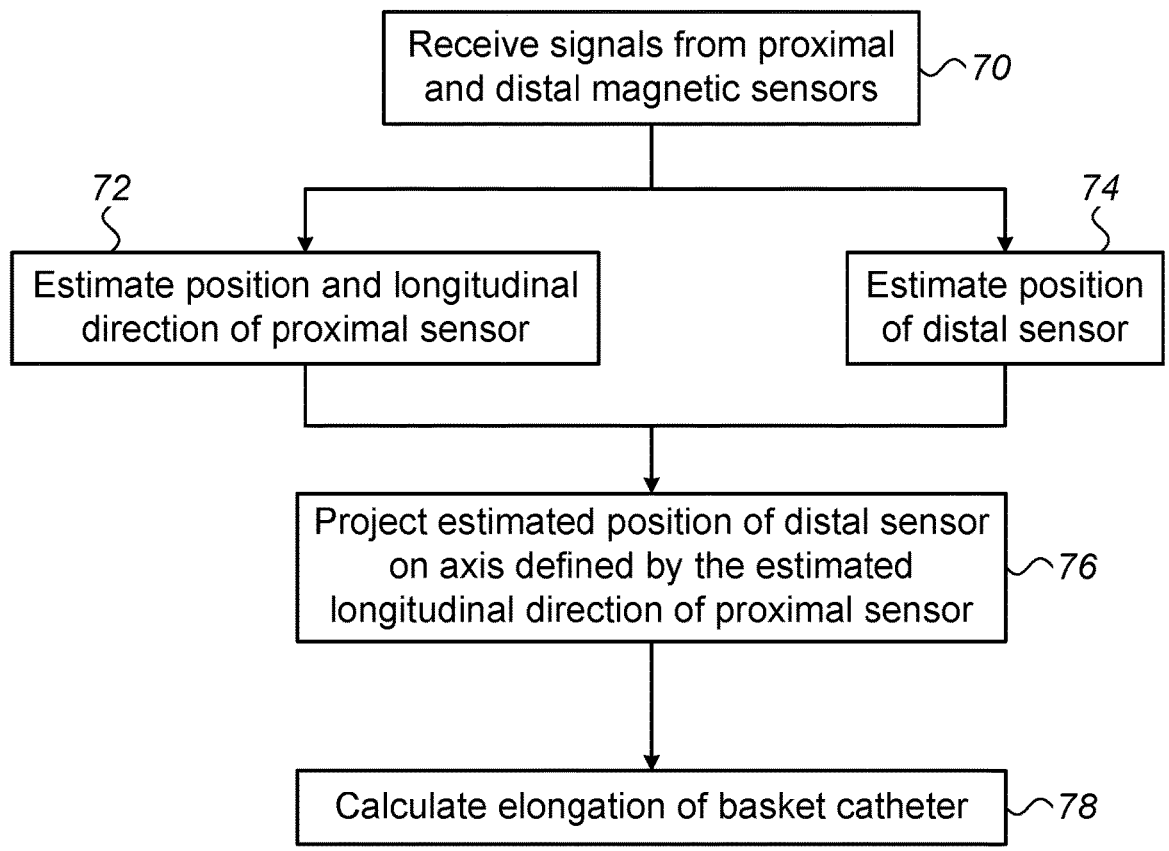
FIG. 3 is a flow chart that schematically illustrates a method and algorithm for estimating basket catheter elongation, in accordance with an embodiment of the present invention.

FIG. 3 is a flow chart that schematically illustrates a method and algorithm for electro-anatomical mapping of a cardiac cavity, in accordance with an embodiment of the present invention. The algorithm, according to the presented embodiment, carries out a process that begins with physician 30 moving basket catheter 40, which is equipped with magnetic sensors 50A and 50B, inside a cardiac cavity.

In an embodiment, as catheter 40 moves within the cardiac cavity, processor 41 receives signals from sensors 50A and 50B, at a signal receiving step 70. Next, based on the signals received from proximal sensor 50A, processor 41 estimates a position and a longitudinal direction of proximal sensor 50A, at a basket proximal measurement step 72. In parallel, based on signals received from distal sensor 50B, processor 41 estimates a respective position of distal sensor 50B, at a basket distal measurement step 74. Next, processor 41 projects any wrongly estimated position 50C of distal sensor 50B, found in step 74, on an axis 62 defined by the estimated longitudinal direction of proximal sensor 50A, at a distal position projection step 76. The aforementioned projected position is marked 50D. Finally, processor 41 calculates the elongation of basket catheter 40, as the distance between position 50A and position 50D, at a basket elongation calculation step 78.

As noted above, based on the calculated elongation, diagnostic and/or therapeutic procedures can be improved, by, for example, correcting assumed positions and orientations of ultrasound transducers fitted over basket catheter 40. Another example is issuing directions to the user to perform an action, based on the calculated elongation, such as to perform elongation of the catheter before inflating the balloon in case the system recognizes that the catheter is in its retracted state.

In some embodiments, processor 41 presents the estimated elongation to physician 30, e.g., using a suitable graphical or textual display on display 27. Additionally or alternatively, processor 41 may adapt the procedure or take any other suitable action autonomously based on the estimated elongation, such as preventing from inflating the balloon in case the balloon catheter is determined by the disclosed technique to be in a retracted state.

The example flow chart shown in FIG. 3 is chosen purely for the sake of conceptual clarity. The flow chart shown in FIG. 3 is applicable, with the necessary changes have been made, to any expandable distal-end assembly of a catheter for insertion into a cavity of an organ of a patient, such as a balloon catheter. The present embodiment also comprises additional steps of the algorithm, such as operating sensors mounted on the basket spines, which have been omitted from the disclosure herein purposely on order to provide a more simplified flow chart.

Although the embodiments described herein mainly address cardiac applications, the methods and systems described herein can also be used in other medical applications in which a catheter is inserted into a cavity of an organ of a patient, such as with a navigable Ear, Nose, & Throat (ENT) probe.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
an expandable distal-end assembly coupled to a distal end of a shaft for insertion into a cavity of an organ of a patient;
a proximal position sensor located at a proximal end of the expandable distal-end assembly;
a distal position sensor located at a distal end of the expandable distal-end assembly; and
a processor, configured to:
based on signals received from the proximal position sensor, estimate a position and a longitudinal direction of the proximal position sensor in a coordinate system used by the processor;
based on signals received from the distal position sensor, estimate a position of the distal position sensor in the coordinate system;
project the estimated position of the distal position sensor on an axis defined by the estimated longitudinal direction; and
calculate an elongation of the expandable distal-end assembly by calculating a distance between the estimated position of the proximal position sensor and the projected position of the distal position sensor.

2. The system according to claim 1, wherein the proximal position sensor and the distal position sensor are magnetic sensors.

3. The system according to claim 1, wherein, using the calculated elongation, the processor is further configured to estimate an ellipticity of the expandable distal-end assembly.

4. The system according to claim 1, wherein the expandable distal-end assembly comprises a basket.

5. The system according to claim 1, wherein the expandable distal-end assembly comprises a balloon.

6. The system according to claim 1, wherein the processor is configured to, based on calculating the elongation, indicate a degree of elongation of the expandable distal-end assembly.

7. A method, comprising:
in a processor, receiving signals from a proximal position sensor located at a proximal end of an expandable distal-end assembly coupled to a distal end of a shaft for insertion into a cavity of an organ of a patient, and from a distal position sensor located at a distal end of the expandable distal-end assembly;
based on the signals received from the proximal position sensor, estimating a position and a longitudinal direction of the proximal position sensor in a coordinate system used by the processor;
based on the signals received from the distal position sensor, estimating a position of the distal position sensor in the coordinate system;
projecting the estimated position on an axis defined by the estimated longitudinal direction; and
calculating an elongation of the expandable distal-end assembly by calculating a distance between the estimated position of the proximal position sensor and the projected position of the distal position sensor.

8. The method according to claim 7, wherein receiving the signals comprises receiving signals from magnetic sensors.

9. The method according to claim 7, and comprising, using the calculated elongation, estimating an ellipticity of the expandable distal-end assembly.

10. The method according to claim 7, wherein the expandable distal-end assembly comprises a basket.

11. The method according to claim 7, wherein the expandable distal-end assembly comprises a balloon.

12. The method according to claim 7, wherein calculating the elongation comprises indicating a degree of elongation of the expandable distal-end assembly.

13. A system, comprising:
an expandable distal-end assembly coupled to a distal end of a shaft for insertion into a cavity of an organ of a patient;
a proximal position device located at a proximal end of the expandable distal-end assembly;
a distal position device located at a distal end of the expandable distal-end assembly, wherein one of the position devices is configured as a transmitter and the other as a receiver; and
a processor, configured to:
based on signals received from the receiver, estimate a distance of the receiver from the transmitter; and
indicate an elongation of the expandable distal-end assembly as a calibrated distance.

14. A method, comprising:
communicating signals between a proximal position device located at a proximal end of an expandable distal-end assembly coupled to a distal end of a shaft for insertion into a cavity of an organ of a patient, and a distal position device located at a distal end of the expandable distal-end assembly, wherein one of the position devices is configured as a transmitter and the other as a receiver;
based on the communicated signals received from the receiver, estimating a distance of the receiver from the transmitter; and
indicating an elongation of the expandable distal-end assembly as a calibrated distance.

* * * * *